(12) United States Patent
Gordils Wallis et al.

(10) Patent No.: US 8,398,643 B2
(45) Date of Patent: Mar. 19, 2013

(54) MAXILLARY BONE CUTTING AND INJECTION SYSTEM AND METHOD OF USING THE SAME

(75) Inventors: Antonio Jose Gordils Wallis, Avenida Felipe Guevara Rojas (VE); Ronald G. Litke, Jr., Danbury, CT (US); Scott Reed, Monroe, CT (US)

(73) Assignee: Innovative Implant Technology, LLC, Aventura, FL (US)

( * ) Notice: Subject to any disclaimer, the term of this patent is extended or adjusted under 35 U.S.C. 154(b) by 506 days.

(21) Appl. No.: 12/685,026

(22) Filed: Jan. 11, 2010

(65) Prior Publication Data

US 2010/0178631 A1 Jul. 15, 2010

Related U.S. Application Data (60) Provisional application No. 61/144,320, filed on Jan. 13, 2009.

(51) Int. Cl.
*A61B 17/00* (2006.01)
(52) U.S. Cl. ........................................................ 606/82
(58) Field of Classification Search .............. 433/75–76, 433/82, 144, 165–166, 197, 226; 606/79–85, 606/92–95; 81/56, 57; 408/7, 12, 14, 15, 408/97, 118, 132, 141, 142; 30/29.5, 276
See application file for complete search history.

(56) References Cited

U.S. PATENT DOCUMENTS

| 4,021,920 | A | * | 5/1977 | Kirschner et al. .............. 433/82 |
| 5,711,315 | A | | 1/1998 | Jerusalmy |
| 5,989,025 | A | | 11/1999 | Conley |
| 7,125,253 | B2 | | 10/2006 | Kitamura et al. |
| 7,250,055 | B1 | * | 7/2007 | Vanderwalle ................... 606/92 |
| 2003/0105469 | A1 | | 6/2003 | Karmon |
| 2003/0175656 | A1 | | 9/2003 | Livne et al. |
| 2006/0084034 | A1 | | 4/2006 | Hochman |
| 2006/0149268 | A1 | | 7/2006 | Truckai et al. |
| 2006/0172255 | A1 | | 8/2006 | Hochman et al. |
| 2006/0265006 | A1 | * | 11/2006 | White et al. ................... 606/232 |
| 2008/0243123 | A1 | * | 10/2008 | Gordils Wallis et al. ....... 606/80 |

FOREIGN PATENT DOCUMENTS

| WO | WO0078371 A1 | 12/2000 |
| WO | WO 2008125449 A1 * | 10/2008 |

* cited by examiner

*Primary Examiner* — Kevin T Truong
*Assistant Examiner* — Diana S Jones
(74) *Attorney, Agent, or Firm* — Gordon & Jacobson, PC (57) ABSTRACT

A bone cutting and injecting device for cutting maxillary bone and injecting a filler through the maxillary bone under a subantral membrane to separate the subantral membrane from the maxillary bone and fill the space formed therebetween. The device includes a hollow tubular element having a diameter sized to be inserted into a pilot hole in the maxillary bone, a piston longitudinally displaceable within the hollow tubular element, and a cutter mounted to the piston and operably disposed adjacent the distal end of the hollow tubular element. A fluid path is defined through the hollow tubular element for guiding the filler, and the cutter is configured to redirect the filler in a transverse or radial direction relative to the longitudinal axis of the tubular element.

23 Claims, 9 Drawing Sheets

MAXILLARY BONE CUTTING AND INJECTION SYSTEM AND METHOD OF USING THE SAME

This application claims the benefit of U.S. Provisional Application No. 61/144,320 filed on Jan. 13, 2009, which is hereby incorporated by reference herein in its entirety.

BACKGROUND OF THE INVENTION

1. Field of the Invention

This invention relates broadly to dental implants. More particularly, this invention relates to a device for removing maxillary bone to access the subantral membrane of the maxillary sinus, dissecting and elevating the subantral membrane, and injecting a filler under the subantral membrane for osseous regeneration to increase the bony support structure therein in preparation for receiving a dental implant.

2. State of the Art

Dental implants have been used in dentistry for about twenty years. They offer a tremendous benefit to patients by allowing for the replacement of missing teeth. The success of a dental implant is based on a variety of factors, including surgical technique, the health of the patient, operator skill, and, to a significant extent, the presence of sufficient bone for the placement and integration of the dental implant. To that end, dental implants are commonly used in the anterior lower jaw as this region provides sufficient bone quantity, quality, and strength to support and hold the dental implant. However, the replacement of the maxillary teeth has presented a considerable challenge because after the loss of maxillary teeth, the quality and quantity of the remaining supporting bone may be insufficient to properly and reliably support the dental implant.

More particularly, the maxillary complex is a three-dimensional bone structure composed of alveolar bone and basal bone. The maxillary teeth, and more specifically the teeth roots, are imbedded in the alveolar bone. The top of the maxillary complex forms the floor of the maxillary sinus and is covered by a thin diaphanous membrane known as the subantral or Schneiderian membrane (referred to herein as the "subantral membrane"). Once a tooth is removed from the maxillary complex, the surrounding alveolar bone is frequently resorbed because of the lack of physical stimulation and support of the teeth. This leads to a loss of bone mass and a corresponding reduction in the effective height and thickness of the bone of the maxillary complex, which if not remedied limits the potential use of the dental implant.

To overcome the deficiency of insufficient vertical bone mass of the maxillary complex, several surgical techniques have been developed to increase available bone mass for the placement of dental implants. These techniques augment the bone deficient region with a filler or regenerative material made of natural and/or artificial (synthetic) materials (collectively, 'bone graft material'). Such material is placed on the roof of the maxillary structure under the subantral membrane so that it does not interfere with the function of the maxillary sinus. Collectively, these procedures are known within the dental profession as "sinus elevation procedures" with the goal of increasing the vertical height available for placement of dental implants. What makes these techniques unique from other techniques, such as distraction osteogenesis, is that the bone is increased within a body cavity, i.e., the maxillary sinus cavity.

Bone augmentation of the maxillary sinus requires careful bone removal and delicate dissection of the subantral membrane from the floor of the sinus. If the membrane is not properly dissected from the bone, bone augmentation may not occur, or may not be sufficient. Unintentional perforation of the subantral membrane may also lead to undesirable short and long-term consequences. If the perforation is large, such as, for example, several millimeters in diameter, the surgeon must either abort the procedure or use some means of removing or containing the bone graft material on the floor of the sinus to encourage new bone growth. Typically, a collagen membrane patch is used to repair the perforation and contain the bone graft material on the floor of the sinus. A lack of integrity of the membrane can also lead to the migration of bone graft materials leading to long-term chronic infections. Therefore, the maintenance of membrane integrity is of utmost importance during the elevation of the membrane to allow placement of bone graft materials with a goal of increasing bone mass in the maxilla.

A commonplace sinus elevation procedure requires a window into the maxillary sinus from a lateral and superior approach to the floor of the sinus. Great care must be taken during the entry to the sinus as it is critical not to perforate the subantral membrane that lines the sinus cavity. Most patients and dental surgeons acknowledge that entrance into the maxillary sinus utilizing a lateral window approach (also known as the Caldwell-Luc procedure) is an invasive procedure. This technique is fraught with many risks and complications because of the limitations of healing potential in the maxillary sinus. In spite of these risks many patients undergo this procedure because of the strong desire to replace missing maxillary teeth with dental implants.

An alternative procedure described by Dr. R. B. Summers approaches the maxillary sinus from the alveolar ridge utilizing solid cylindrical osteotomes. It is a more conservative approach and is less invasive. The technique vertically lifts the subantral membrane from the floor of the maxillary sinus via an infracture of the bony floor. The infracture can be performed using solid cylindrical osteotomes with specific diameters that are vertically advanced toward the maxillary sinus producing a mechanical lifting action on the membrane. Bone graft material is then placed into this space for bone augmentation. The bone graft materials are actually used to raise the subantral membrane. While this technique is safer than the lateral window approach, an overzealous use of an osteotome during the procedure can result in the perforation of the subantral membrane with the disadvantages discussed above.

U.S. Patent Pub. No. 2006/0084034 to Hochman discloses a method and apparatus for providing implants in the upper jaw of a person. The apparatus includes one or more sleeves having various lengths and diameters, each preferably including a tip for cutting a hole into the maxillary bone underneath the subantral membrane. The sleeve is hollow to allow fluid (gas, air, powder, paste, gel, or liquid) to be inserted under the membrane to cause it to lift from the sinus floor.

U.S. Patent Pub. No. 2006/0172255 to Hochman discloses a surgical tool having a fluid communication passageway that allows a fluid to be pumped into the tool at a defined pressure to displace the sinus membrane without compromising or tearing the membrane, thereby pushing the sinus membrane in an upward direction and creating a newly formed cavity space. The fluid passageway connects with radially extending holes through the shaft of the tool to allow fluid to pass therethrough.

In the prior art techniques discussed above, advancing a bone cutter through the maxillary bone with insufficient control or feedback and/or injecting bone graft materials in an axial direction under the subantral membrane after such uncontrolled cutting and lifting may result in tearing or ripping of the subantral membrane. Overcoming these previous limitations in the technique of sinus elevation will reduce infection, bleeding, swelling, pain, suffering and failure when using dental implants in the maxillary sinus.

SUMMARY OF THE INVENTION

The present invention provides a device and methodologies for drilling maxillary bone to access the subantral membrane, separating and dissecting the subantral membrane from the floor of the maxillary sinus, and implanting bone, bone substitutes, and/or an osseogenic material under the subantral membrane. The device includes a hollow tubular element fixed at a proximal end within an upper drive body. A hollow piston extends through the hollow tubular element. The distal end of the piston is rotatably fixed to a cutter, which is adapted to cut through maxillary bone and operably disposed adjacent the distal end of the hollow tubular element. The proximal end of the piston is fixed to a distal end of an upper drive shaft. The upper drive shaft extends through the upper drive body and an adjacent lower drive body, both of which are used to forcibly rotate and advance the device through maxillary bone as further discussed below. The device also includes a lower drive shaft which is fixed at a proximal end to the lower drive body, engagable at a distal end with the upper drive shaft, and extends at least partially through the upper and lower drive bodies. The cutter, piston, and upper drive shaft are longitudinally displaceable relative to the hollow tubular element, lower drive shaft, and upper and lower drive bodies. A spring disposed between gears on the upper and lower drive shafts biases the cutter, piston, and upper drive shaft toward a distal position.

The hollow tubular element has an outer threaded surface that engages and rotatably advances into bone when the upper drive body is forcibly rotated. In the distal position, the cutter extends beyond the distal end of the hollow tubular element by a first displacement distance. The device achieves the distal position when the force of the spring bias is greater than the load on the cutter. When the load on the cutter is greater than the spring bias, the cutter, piston, and upper drive shaft are longitudinally translated in a proximal direction by, at most, the first displacement distance relative to the tubular element, lower drive shaft, and upper and lower drive bodies. The upper and lower drive bodies of the device are optionally adapted to receive one or more torque applying tools for rotating and/or stabilizing the device as it is advanced or withdrawn from the maxillary bone.

The device is fluidly connectable to a filler source such that bone, bone substitutes, and/or osseogenic material in a flowable carrier (hereinafter, "filler") may be injected through the device to an area under the subantral membrane. In the preferred embodiment, filler is injected up and through the upper drive shaft, up and through the piston, through the cutter at the distal end of the tap, to an area between the floor of the maxillary sinus cavity and the sinus membrane to separate the sinus membrane from the floor. The cutter preferably defines openings for directing the filler in a direction transverse to the longitudinal axis of the tubular element. The device is thus used as both a bone cutter and filler injector.

In other embodiments, the piston defines external channels or flutes such that the filler exits the piston adjacent the cutter and is directed by the cutter toward an area between the floor of the maxillary sinus and the subantral membrane. In yet other embodiments, the upper drive shaft defines holes at a distal end for directing filler around the piston, and guiding it via the inner wall of the tubular member toward the cutter, where it exits the tubular element and is guided by the blades of the cutter in a direction transverse to the longitudinal axis of the tubular element.

Prior to operation of the device, the gingiva is opened to reveal the underlying maxillary bone at the location of an intended dental implant. A hole is marked in the bone with a burr, a small pilot hole is preferably drilled to within preferably approximately 1 to 2 mm of the subantral membrane, and a preferably 3.2 mm drill bit is used to enlarge the hole to such diameter also to within preferably approximately 1 to 2 mm of the subantral membrane. The device is then inserted into the entrance of the pre-drilled hole and torque is applied to the upper drive body to forcibly rotate and advance the threaded tubular element into the hole. When the device reaches the closed end of the pre-drilled hole, bone at the end of the hole pushes the cutter from the unloaded configuration against the spring-bias toward the distal end of the tubular element (thereby decreasing or eliminating the first displacement distance) into a loaded configuration. In the loaded configuration, a gear situated on the upper drive shaft is engaged with a gear situated on the lower drive shaft, which is fixed at its proximal end to the lower drive body. Torque applied to the lower drive body then forcibly rotates the cutter and threaded tubular element, and advances the device beyond the end of the pre-drilled hole.

When the cutter breaks through the bone just under the subantral membrane, the proximal force on the cutter by the bone material, or lack thereof, becomes less than the bias of the spring. The cutter is thus moved distally relative to the hollow tubular element by the spring, back into the distal position. The relative distal movement of the cutter when it reaches the subantral membrane is no more than the first displacement distance, which is not enough to breach or damage the subantral membrane. The cutter cannot move more than the first displacement distance relative to the hollow tubular element because of interference between the upper drive shaft to which it is connected and the upper drive body. The first displacement distance is enough to slightly lift the subantral membrane. In addition, the distal movement of the cutter, piston, and upper drive shaft by the spring causes the gear on upper drive shaft to disengage from the gear on the lower drive shaft to the extent that the lower drive body and lower drive shaft freely rotate and cannot advance the cutter. The free rotation of the lower drive body gives notice to the user that he or she has reached the subantral membrane. The disengagement of the gears precludes distal advancement of the device by the lower drive body.

In the preferred embodiment, a fill line connector is provided to the proximal end of the device. Filler is preferably injected through the device and exits at a distal end of the device at an area under the subantral membrane as discussed above. After sufficiently injecting filler under the subantral membrane, the device is removed from the hole in the maxillary bone by forcibly rotating the upper drive body in a direction opposite from insertion, which rotatably withdraws the device. The gingiva may be closed temporarily for healing at this time. Alternatively, a drill corresponding to the anchor of the intended implant is used to drill a hole of corresponding diameter, the implant is placed therein, and the gingiva is closed thereover.

Additional features and advantages of the invention will become apparent to those skilled in the art upon reference to the detailed description taken in conjunction with the provided figures.

DETAILED DESCRIPTION OF THE PREFERRED EMBODIMENTS

Turning to FIGS. 1-4, a bone cutting device 10 adapted to remove maxillary bone, dissect the subantral membrane from the floor of the maxillary sinus, and receive bone filler for injection underneath the subantral membrane is shown and now described. The device 10 includes a hollow tubular element 12, a hollow piston 14, a cutter 16, upper and lower drive bodies 20, 22, hollow upper and lower drive shafts 26, 28, a spring 44, and a syringe coupler 50.

Figure 1:
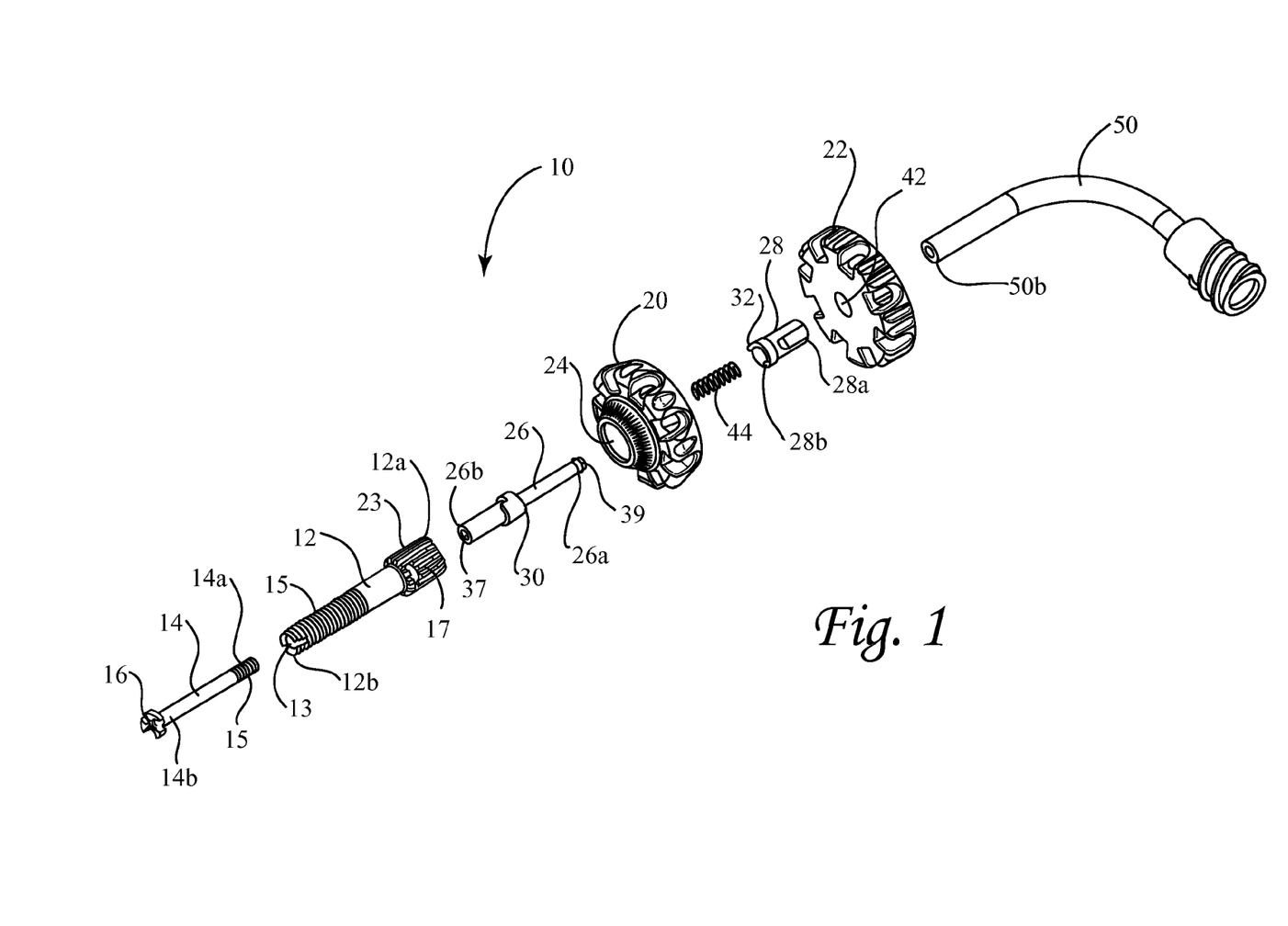
FIG. 1 is a longitudinally exploded view of a bone cutter device and syringe coupler according to the invention.
Figure 2:
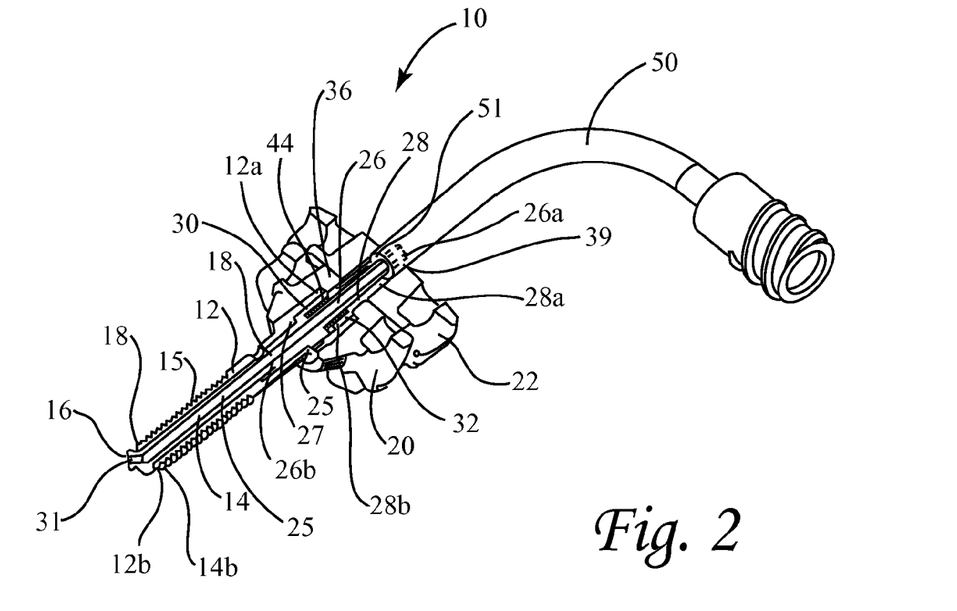
FIG. 2 is an assembled longitudinal sectional view of the bone cutter device of FIG. 1 with the syringe coupler shown attached.
Figure 3:
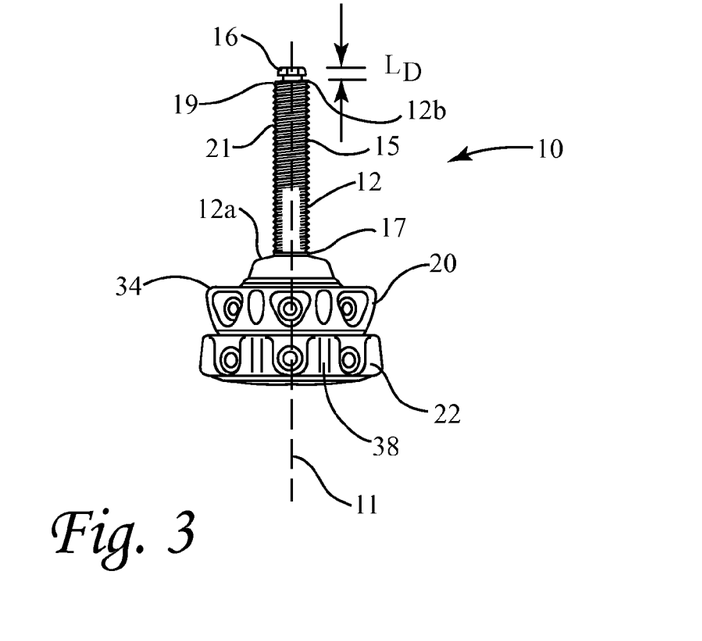
FIG. 3 is a side view of the bone cutter device of FIG. 1.

The hollow tubular element 12 is best seen with reference to FIGS. 1-3. The tubular element 12 extends from a proximal end 12a fixed within the upper drive body 20, through a bore 24 defined by the upper drive body 20, to a distal end 12b. The tubular element 12 defines an inner bore 13 between the proximal and distal ends 12a, 12b, and includes a tap (an outer threaded surface) 15 that extends from the distal end 12b toward the proximal end 12a, and a barrel 17 at the proximal end 12a. The tap 15 is engageable and rotatably advanceable into bone, and includes distal cutting flutes 19 (FIG. 3) and self-tapping threads 21 (FIG. 3). The barrel 17 is provided with longitudinal ridges 23 that are preferably interference fit into the bore 24 of the upper drive body 20. The barrel 17 may also be fixed into the upper drive body 20 via bonding or other means. The tubular element 12 also includes inner flanges 25, 27 (FIG. 2) near the proximal end 12a, which operate as a stop as further discussed below with respect to the upper drive shaft 26.

The hollow piston 14 extends through and is longitudinally displaceable within the inner bore 13 of the hollow tubular element 12. A cutter 16 is mechanically coupled to a distal end 14b of the piston 14, and operably disposed adjacent the distal end 12b of the hollow tubular element 12. The piston 14 and cutter 16 are best seen with reference to FIG. 4. The piston 14 has threads 29 at the proximal end 14a, and a diameter smaller than that of the cutter 16. The cutter 16 preferably includes three cutting blades 16a, 16b, 16c structurally adapted to remove maxillary bone. The blades of the cutter 16 are angled so that the cutter 16 is slightly "dished" to cut at the circumferential edges first, similar to a hole saw. This enables the cutter 16 to cut a disc of bone, and helps prevent the radial edges of the blades from contacting the subantral membrane during use of the device 10 as further discussed below. The three cutting blades 16a, 16b, 16c each define openings 31 (FIGS. 2, 4) extending from an upper surface 33 of the cutter 16 through the respective cutting blades 16a-c. The openings 31 are in fluid communication with an inner channel 25 (FIGS. 2, 4) defined by the hollow piston 14, and thus angle radially inward from the upper surface 33 to the inner channel 25.

The hollow upper and lower drive shafts 26, 28 are best seen with reference to FIGS. 1-2. The upper drive shaft 26 has inner threads 37 at a distal end 26b which mate with the threads 29 at the proximal end 14a of the piston 14, rotatably and longitudinally fixing the hollow upper drive shaft 26 to the piston 14. The upper drive shaft 26 extends from the distal end 26b through the upper drive body 20, the hollow lower drive shaft 28, and an adjacent lower drive body 22 to a proximal end 26a. At the proximal end 26a, the upper drive shaft 26 preferably includes a flexible engagement structure such as barbs 39 or equivalents thereof for coupling to the inside of the distal end 50b of the syringe coupler 50. The flexible engagement structure 39 may instead be mounted within the bore 42 of the lower drive body 22 instead of being attached to the upper drive shaft 26.

The hollow lower drive shaft 28 is fixed at a proximal end 28a within a bore 42 extending through the lower drive body 22, and extends at least partially through the upper and lower drive bodies 20, 22. Gears 30, 32 are provided to the external surfaces of the upper and lower drive shafts 26, 28 for detachable engagement to rotatably connect the upper and lower drive shafts 26, 28 during use of the device 10 as further discussed below.

The upper and lower drive bodies 20, 22 are best seen with reference to FIGS. 1-3. The upper drive body 20 extends radially outward relative to a longitudinal axis 11 of the hollow tubular element 12 and provides substantial surface area and ergonomics for manual rotation, including external gripping ridges 34. An inner flange 36 (FIG. 2) within the upper drive body 20 operates as a stop to prevent proximal movement of the tubular element 12 relative to the upper drive body 20 when under load. Inner flanges 25, 27 (FIG. 2) near the proximal end 12a of the tubular element 12 operate as a stop limit the distal movement of the gear 30, and thus the upper drive shaft 26, relative to the tubular member 12. As discussed above, the proximal end 12a of the tubular element 12 is fixed within a bore 24 extending through the upper drive body 20 by an interference fit. In addition, the upper drive body 20 is rotatably coupled to the upper drive shaft 26 via the tubular element 12 and gear 30 (FIG. 2). Thus, rotation of the upper drive body 20 rotates the tubular element 12, upper drive shaft 26, piston 14, and cutter 16.

The lower drive body 22 also extends radially outward relative to the longitudinal axis 11 and provides substantial surface area and ergonomics for manual rotation, including external gripping ridges 38. As discussed above, the proximal end 28a of the lower drive shaft 28 is fixed within the bore 42 of the lower drive body. Thus, when the gears 30, 32 of the upper and lower drive shafts are unengaged, rotation of the lower drive body rotates the lower drive shaft 28. When the gears 30, 32 are engaged, rotation of the lower drive body 22 rotates the upper and lower drive shafts 26, 28, the tubular member 12, the upper drive body 20, the piston 14, and the cutter 16. The bore 42 of the lower drive body 22 is adapted to receive the syringe coupler 50, which preferably detachably couples to the barbs or other flexible engagement structure 39 mounted to the proximal end 28a of the upper drive shaft 28 and/or within the bore 42 of the lower drive body 22.

The spring 44 is best seen with reference to FIGS. 1-2. The spring 44 is preferably a coil spring disposed inside the bore 24 of the upper drive body 20 between the gears 30, 32 of the upper and lower drive shafts 26, 28. The spring 44 biases gears 30, 32 toward an unengaged position (FIG. 2). When the force placed on the cutter 16 is less than the bias force of the spring on the gear 30 of the upper drive shaft 26, the spring 44 moves the cutter 16, piston 14, and upper drive shaft 26 (which move together longitudinally) by no more than a first displacement distance $L_D$ (FIG. 3) in a distal direction relative to the hollow tubular element 12, lower drive shaft 28, and upper and lower drive bodies 20, 22. This longitudinal displacement is limited to the first displacement distance $L_D$ because the gear 30, which is fixed to the outer surface of the upper drive shaft 26, is stopped by the flanges 25, 27 (FIG. 2) inside the tubular element 12 (e.g., as shown in FIG. 2, the distance between the flange 36 of the upper drive body 20 and the flange 27 of the tubular element 12 limits the longitudinal distance by which the gears 30, 32 can separate).

The operation of the device 10 to cut maxillary bone and advance it toward the subantral membrane is substantially similar to that disclosed in U.S. application Ser. No. 11/853, 082 and International Application Number PCT/US2008/ 057421, which are incorporated by reference herein in their entireties. More particularly, in operation, the gingiva is opened to reveal the underlying maxillary bone at the location of an intended dental implant. A hole is preferably marked in the bone at the location with a dental burr, a small pilot hole is preferably drilled in the bone to within preferably approximately 1 to 2 mm of the subantral membrane, and a preferably 3.2 mm drill bit (or drill, used interchangeably) is used to enlarge the hole to such diameter also to within preferably approximately 1 to 2 mm of the subantral membrane. A 3.2 mm drill bit is preferred, as it corresponds with the tap dimension, is suitable for curette passage and approximates the dimension of an anchor of a dental implant at the conclusion of the procedure.

Figure 5:
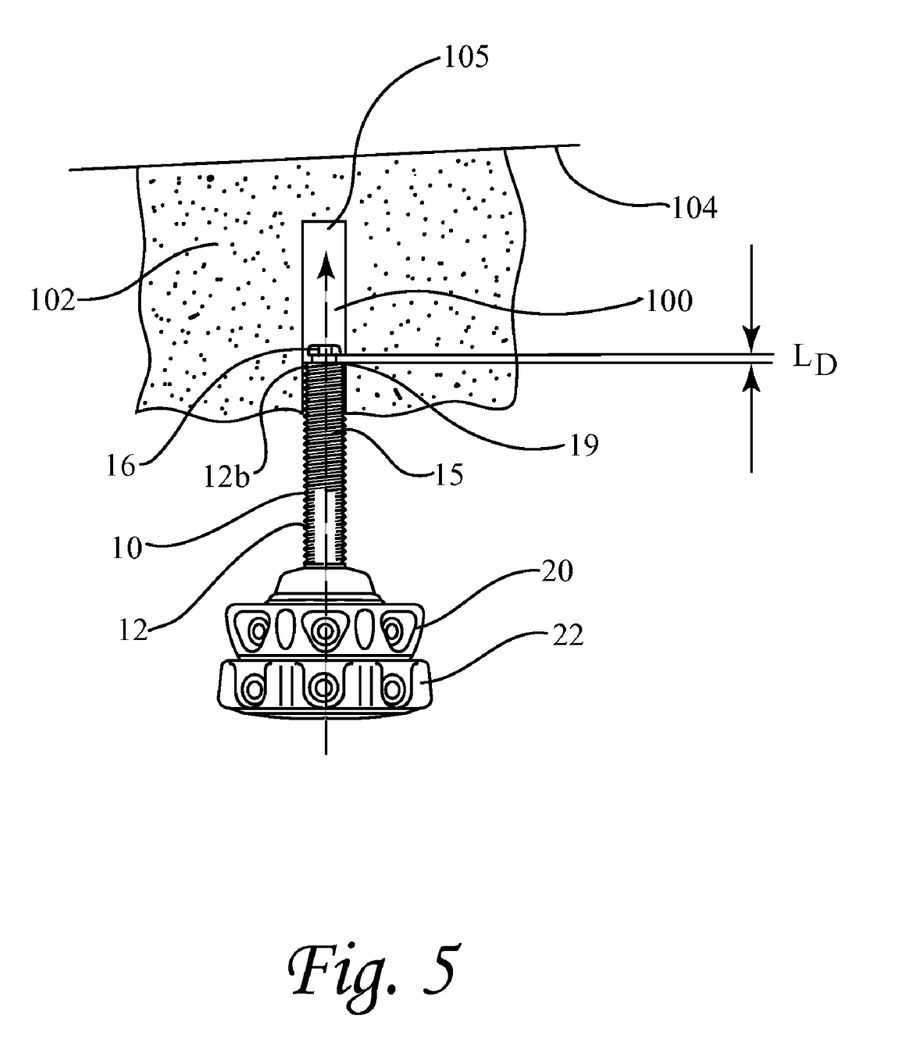
FIG. 5 illustrates use of the bone cutter device of FIG. 1 with the tubular element disposed inside the entrance of a pilot hole in the maxillary bone and the cutter disposed in an unloaded configuration.
Figure 6:
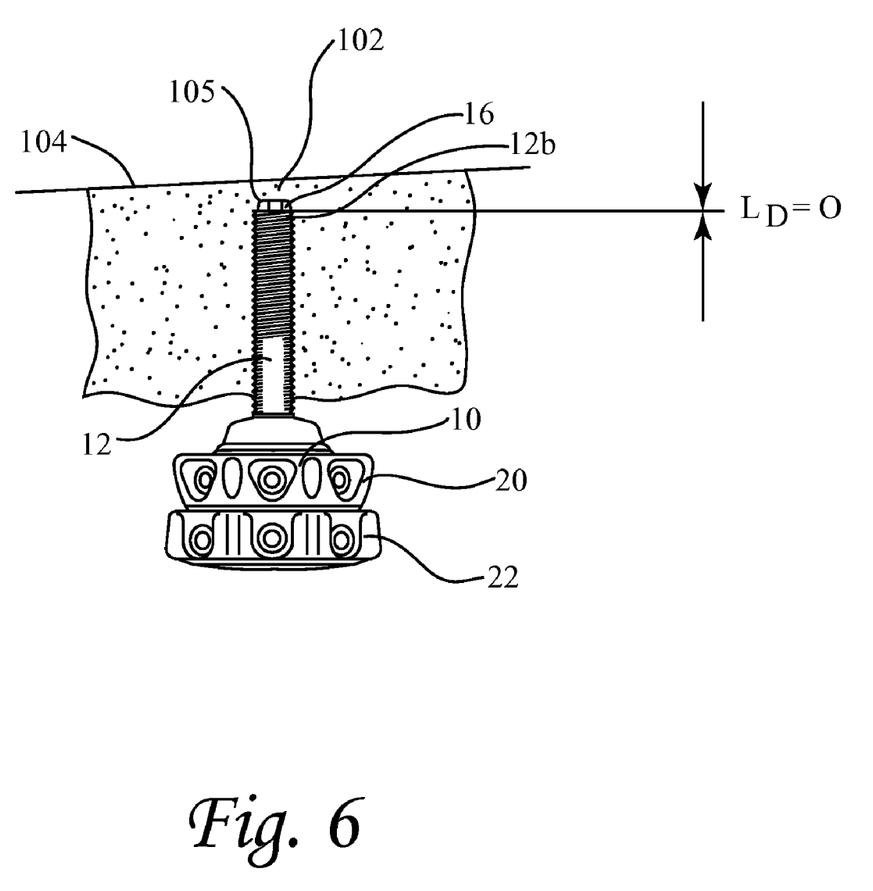
FIG. 6 illustrates use of the bone cutter device of FIG. 1 with the tubular element disposed at the end of the pilot hole in the maxillary bone and the cutter disposed in a loaded configuration.
Figure 7:
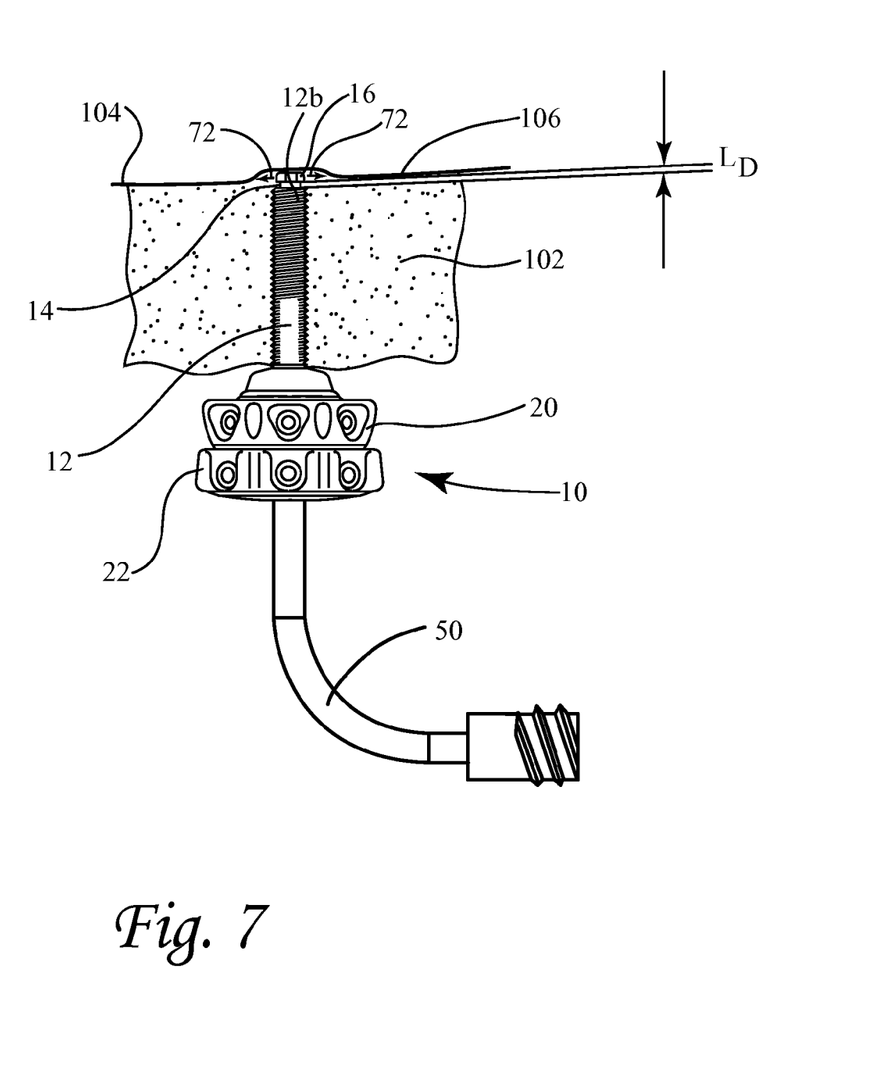
FIG. 7 illustrates use of the bone cutter device of FIG. 1 with the tubular element disposed inside the maxillary bone, the cutter disposed at the subantral membrane in an unloaded configuration, and the syringe coupler attached to the device.

The advancement of the device 10 toward the subantral membrane is best seen with reference to FIGS. 5-7 and occasional reference to FIGS. 1-2. Turning to FIG. 5, the device 10 is inserted into a pre-drilled hole 100 in the maxillary bone 102 under the subantral membrane 104. As discussed above, the upper drive body 20 is rotatably fixed to the hollow tubular element 12. Thus, as torque is initially applied to the upper drive body 20, the distal cutting flutes 19 of the tap 15 grasp and cut into the maxillary bone 102, and the device 10 is advanced distally toward the end 105 of the pre-drilled hole 100. At this point, the cutter 16 is unloaded inside the hole 100 and the bottom of the cutter 16 extends beyond the distal end 12b of the tubular element 12 by a distance $L_D$. In this unloaded configuration, the gear 30 of the upper drive shaft 26 is disengaged from the mating gear 32 on the lower drive shaft 28 by the bias of the coil spring 44 (FIGS. 1-2). Thus, it is noted that in this unloaded configuration, rotation of the lower drive body 22 will only cause rotation of the lower drive shaft 28, not the upper drive shaft 26, piston 14, or cutter 16.

Turning to FIG. 6, the upper drive body 20 is rotated until the cutter 16 reaches the end 105 of the pilot hole 100. At this point, the user will feel increased resistance on the upper drive body 20. This is because the end 105 of the hole has been reached and the user feels the resistance of the maxillary bone 102 disposed beyond the cutter 16 and tubular element 12. The forcible rotation of the upper drive body 20 coupled with the resistance of the maxillary bone 102 on the cutter 16 forces the cutter 16 to move proximally toward the distal end 12b of the tubular element 12. The piston 14 and upper drive shaft 26 (FIGS. 1-2) move proximally with the cutter 16 relative to the tubular element 12, and the gear 30 on the upper drive shaft 26 is forced against the bias of the spring 44 to engage the gear 32 on the lower drive shaft 28 (FIG. 2). These movements cause the device 10 to achieve the loaded configuration of FIG. 6 in which the displacement distance $L_D$ has been eliminated.

With the gears 30, 32 now engaged, user rotation of the lower drive body 22, which previously only caused rotation of the lower drive shaft 28 (FIG. 2), now causes rotation of both the upper and lower drive shafts 26, 28, which drives rotation of the piston 14 and cutter 16. It is appreciated that the gears 30, 32 (FIGS. 1-2) may be modified such that a varying amount of rotation of the lower drive body 22 may be required before the gears 30, 32 engage once the cutter 16 is in the loaded configuration. The forcible rotation of the cutter 16 causes it to cut into the maxillary bone 102 beyond the end 105 of the hole 100, and the device 10 once again advances distally toward the subantral membrane 104. It is noted that in this loaded configuration, rotating the lower drive body 22 also causes rotation of the upper drive body 20 on account of the interference fit between the upper drive shaft 28 and the tubular element 12, and between the tubular element 12 and the upper drive body 20. It is also noted that in this loaded configuration, the user should only forcibly rotate the lower drive body 22 because the resistance on the lower drive body 22 will substantially decrease when the cutter 16 reaches the subantral membrane 104 as discussed below, and thus alert the user that it has been reached.

Turning to FIG. 7, once the cutter 16 cuts through the maxillary bone 102 and reaches the subantral membrane 104, the force on the cutter 16 is substantially reduced, and the bias of the spring 44 causes the upper drive shaft 26 to move distally relative to the lower drive shaft 28, which separates the gear 30 on the upper drive shaft 26 from the gear 32 on the lower drive shaft 28 (FIGS. 1-2). The distal movement of the upper drive shaft 26 causes distal displacement of the piston 14 and cutter 16 relative to the distal end 12b of the tubular element 12, which lifts the subantral membrane 104 off of the maxillary bone 102 by the first displacement distance $L_D$. In the preferred embodiment, $L_D$ is approximately 0.75 millimeters. The cutter 16 cannot move the subantral membrane 104 more than the displacement distance $L_D$ because, as discussed above, the flanges 25, 27 (FIG. 2) of the tubular element 12 limit the distal displacement of the upper drive shaft 26 by acting as a stop against which the gear 30 abuts. Such displacement is not great enough to cause perforation or any damage to the membrane 104. Moreover, the slight lifting of the membrane 104 facilitates subsequent 'lifting' procedures to prepare the membrane 104 for receiving bone graft materials for implant support as further discussed below.

With the gears 30, 32 now separated again, rotation of the lower drive body 22 will only rotate the lower drive shaft 28 and will not cause the device 10 to advance distally. In addition, the user will feel the decreased resistance on the lower drive body 22 and recognize that the subantral membrane 104 has been reached. After the hole is cut through the maxillary bone 104 and the subantral membrane 104 has been reached, the syringe coupler 50 is connected to the proximal end 26a of the upper drive shaft 26 and/or the lower drive body 22 (FIGS. 1-2) via the barbs or other equivalent structure 39. The syringe coupler 50 may also attach to the device 10 by other equivalent engagement structure. The syringe coupler 50 also optionally passes through a portion of the central bore 42 (FIG. 1) of the lower drive body 22 and is optionally fixed therein by a press fit coupling—e.g., the outer wall 51 (FIG. 2) of the syringe coupler 50 may be press fit and fluidly sealed into the space defined by the bore 42 of the lower drive body 22 and the outer surface of the proximal end 26a of the upper drive shaft 26.

Figure 4:
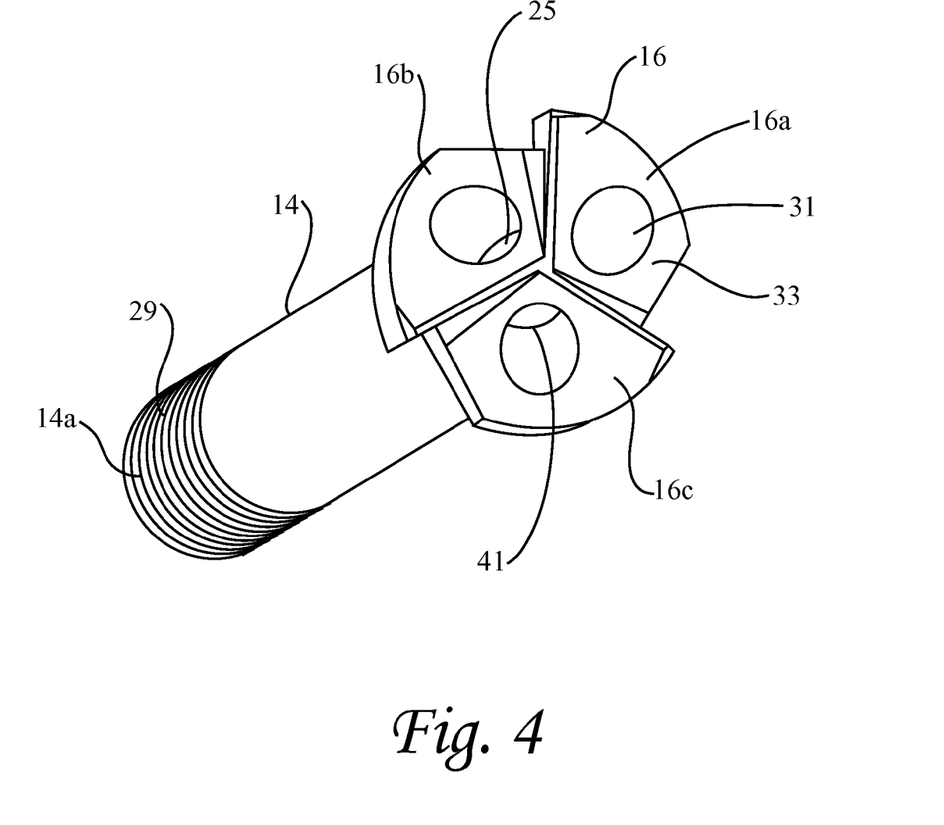
FIG. 4 is an enlarged view of the cutter and piston of FIG. 1.

Bone filler is injected from a syringe (not shown) through the syringe coupler 50, through the upper drive shaft 26 (which extends through the lower drive shaft 28), preferably through the inner channel 25 of the piston 14, and preferably through and out holes 31 in the cutter 16 (FIGS. 2, 4). Thus, a fluid coupling seal is preferably achieved between the threads 29, 27 (FIG. 1) of, respectively, the proximal end 14a of the piston 14 and the distal end 26b of the upper drive shaft 26.

The filler travels through the inner channel 25 of the hollow piston 14 (FIGS. 2 and 4), and at the distal end 14b of the piston 14, enters the openings 31 defined by the cutting blades 16a-c of the cutter 16. The openings 31, which extend from the upper surface 33 of the cutter 16 to the internal channel 25, preferably redirect the longitudinal flow of the filler around a bend 41 (FIG. 4) in each cutting blade such that the filler exits the blades 16a-c in a transverse, and preferably radial direction relative to the longitudinal axis 11 of the tubular element 12. The filler thus exits the cutter 16 in the direction shown by the arrows 72 in FIG. 7. The injection of the filler in a radially transverse direction causes increased pressure on the sides of the cutter 16 as the filler builds up between the maxillary bone 102 and the subantral membrane 104, which causes separation and lifting of the subantral membrane 104 from the floor 106 of the maxillary sinus. As additional filler is injected, the subantral membrane 104 is lifted even further and the filler flows in a lateral direction in the area between the floor 106 and the membrane 104. Thus, the subsequent lifting of the membrane 104 is caused by the pressurized filler, which distributes the lifting force placed on the membrane 104 over an increased surface area. This is in distinction from the force distribution of standard instruments or tools known in the art for raising the subantral membrane 104, where all or a majority of the force is directed axially, leading to significant pressure on the membrane 104 which can result in membrane rupture.

After sufficiently injecting filler under the subantral membrane 104, the device 10 is simply removed from the maxillary bone 102 by forcibly rotating the upper drive body 20 in a direction opposite from insertion. The gingivia may be closed for healing at this time. Alternatively, a drill corresponding to the anchor of the intended implant is used to drill a hole of corresponding diameter, the implant is placed therein, and the gingivia is closed thereover.

Figure 8:
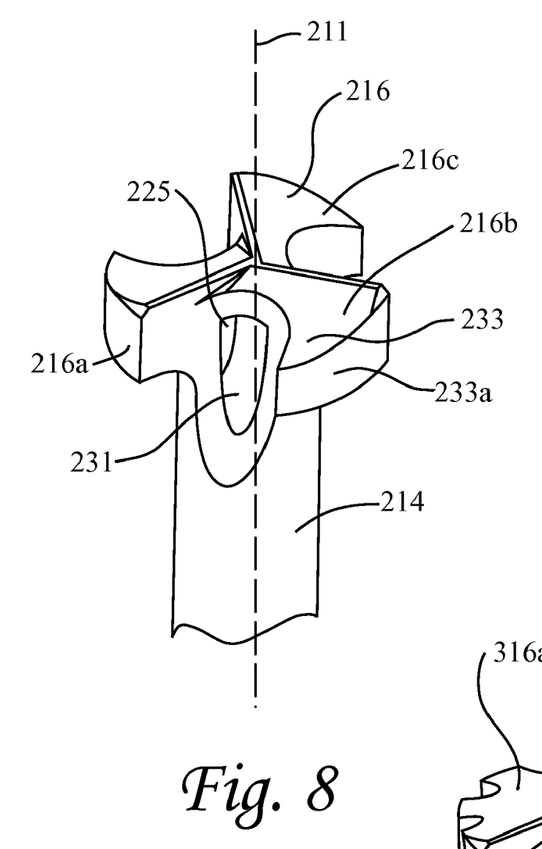
FIG. 8 is a view of a second embodiment of the device according to the invention with an alternative cutter and piston design.

In other embodiments, the device 10 may be formed with alternative cutter designs. Turning to FIG. 8, a second embodiment of the cutter 216 and piston 214 is shown. In this embodiment, the openings 231 are in fluid communication with the internal channel 225 of the piston 214, but are defined by both the cutting blades 216a-c and the piston 214. In addition, the openings 231 extend through both the upper surface 233 and side surface 233a of the respective cutting blades 216a-c, which helps to direct the filler in a more perpendicular direction relative to the longitudinal axis 211 of the tubular element.

Figure 9:
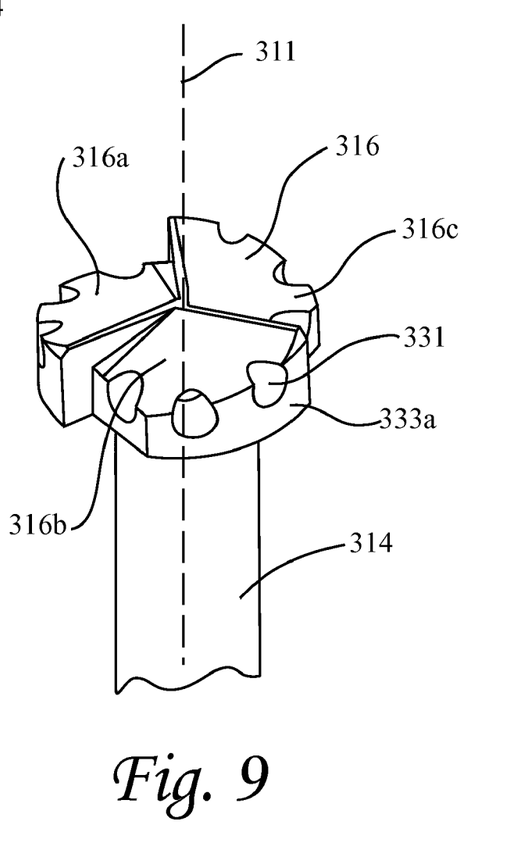
FIG. 9 is a view of a third embodiment of the device according to the invention with yet another alternative cutter and piston design.

Turning to FIG. 9, a third embodiment of the cutter 316 and piston 314 is shown. In this embodiment, multiple smaller openings 331 are defined by each cutting blade 316a-c and extend in a direction substantially parallel with the direction of the cutting blades from their respective side surfaces 333a to the internal channel (not shown) of the piston. This embodiment allows for more principally radial injection of bone materials and decreased axial projection of bone materials relative to the longitudinal axis 311 of the tubular element.

Figure 10:
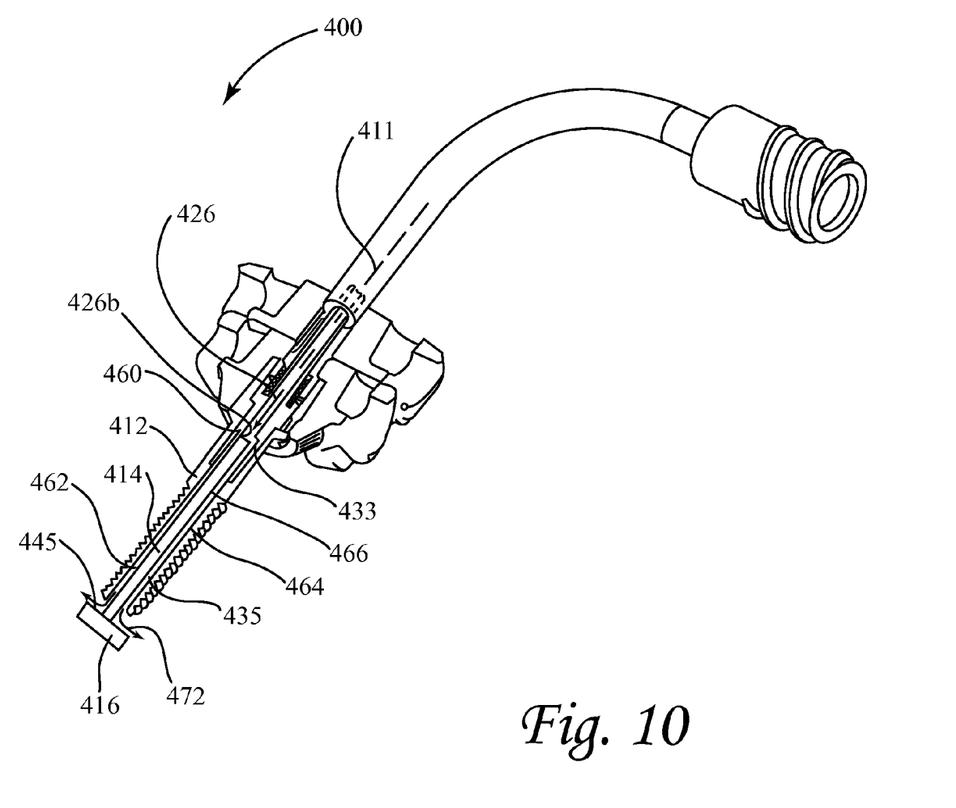
FIG. 10 is a view of a fourth embodiment of the device according to the invention with an alternative flow path design.

In other embodiments, the device 10 may be formed with alternative flow paths. Turning to FIG. 10, a fourth embodiment of the device 400 is shown according to the present invention in which the piston 414 is solid and the upper drive shaft 426 defines holes 460 at the distal end 426b for directing filler around the piston 414. The filler flows through the holes 460, and through the annular space 462 defined by the inner surface 464 of the tubular element 412 and the outer surface 466 of the piston 414. The filler is thus guided toward the cutter 416, which may be designed according to any of the embodiments discussed above or equivalents thereof. When the filler exits the tubular element 412, it is blocked by the bottom surface 445 of the cutter 416 (e.g., the bottom of the cutter blades) and is directed by the resulting longitudinal buildup in pressure coupled with the blockage created by the cutter 416 in a direction transverse to the longitudinal axis 411 of the tubular element 412 as shown by the arrows 472.

Figure 11:
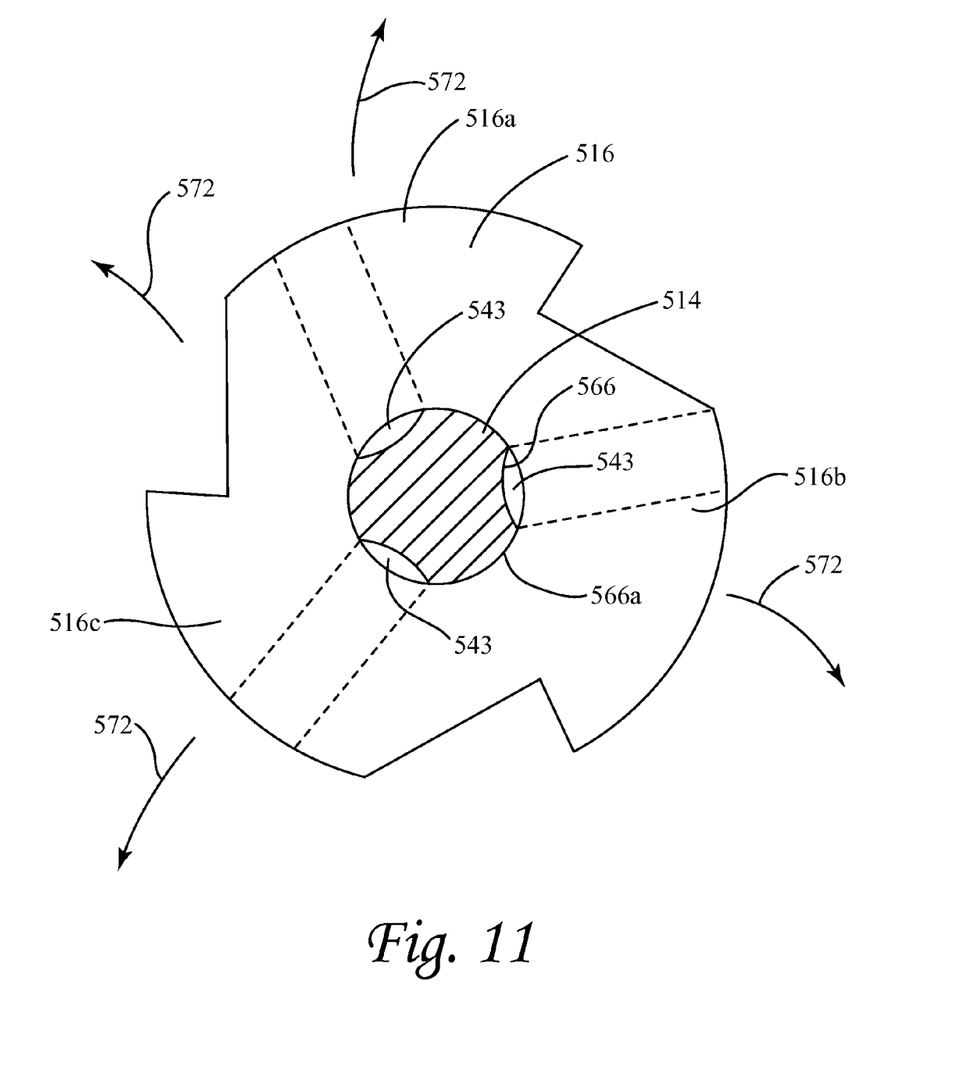
FIG. 11 is a view of the proximal end of a fifth embodiment of the piston and cutter of the invention with the piston defining external flutes or channels.

Turning to FIG. 11, a section view in the distal direction of a fifth embodiment of the piston 514 and cutter 516 is shown. The piston 514 is solid and defines external flutes or channels 543 in fluid communication with the interior of the hollow upper drive shaft (not shown). The piston 514 of FIG. 11 may be used in lieu of the piston of the other embodiments, in which case the filler flows from the upper drive shaft, through the flutes 543, bounded by the outer surface 566 of the piston 514 and the inner surface of the tubular member (not shown), directly into the holes of the cutter 516 (which are preferably aligned with the flutes 543 of the piston 514), and exits the device through the cutter blades 516a-c in a direction transverse to the longitudinal axis of the tubular member as shown by the arrows 572. Alternatively, the piston 514 of FIG. 11 may be used in lieu of the piston shown in FIG. 10, in which case the filler flows from the upper drive shaft, along both the flutes 543 and the annular space defined by the inner surface of the tubular element (not shown) and the non-fluted portion 566a of the outer surface of the piston 514, and out of the tubular element (not shown), where it is directed by the bottom surface of the cutter 516 in the direction indicated by the arrows 572.

In all of the embodiments, the upper and lower drive bodies of the device may be adapted to receive torque applying tools or torque sticks according to the various embodiments disclosed in U.S. application Ser. No. 11/853,082 and International Application Number PCT/US2008/057421, which have been incorporated by reference in their entireties.

All components of the embodiments of the device are preferably made of metal or metal alloys and/or one or more suitable hard polymeric materials or ceramic. It is especially preferable that the cutting element be made of metal, metal alloy or ceramic, or coated with a ceramic.

While the bone cutting and injecting device has been described with respect to performing bone removal on the maxillary bone and injection of bone materials under the subantral membrane, it is appreciated that the device may have utility in other surgical procedures. For example, the device may be used to manually cut a bone in cranial procedures for access to the space within the cranium, e.g., for nerolosurgical procedures. In addition, the device may be used for spinal procedures to access the space within the spinal column. Furthermore, the device may be used for ontological procedures to access the middle ear for ossicular repair or for ossicular prosthesis implantation. For the various procedures, it is appreciated that the device may be provided in dimensions suitable for the respective procedures.

There have been described and illustrated herein embodiments of a bone cutting and injecting device and methodologies for using the same. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its scope as claimed.

What is claimed is:

1. A bone cutting device for cutting maxillary bone and injecting a filler through the maxillary bone and under a subantral membrane to separate the subantral membrane from the maxillary bone and fill the space formed therebetween, the device comprising:
   a) a hollow tubular element having a diameter sized to be inserted into a pilot hole in the maxillary bone, said tubular element including a proximal end, a distal end opposite said proximal end, a longitudinal axis, and a threaded exterior surface configured to be threadedly advanced into the pilot hole;
   b) a piston longitudinally displaceable within said hollow tubular element; and
   c) a cutter mounted to said piston and operably disposed adjacent said distal end of said hollow tubular element, said cutter having at least one cutting blade wherein said cutter is spring biased into a distally displaced position relative to said distal end of said hollow tubular member, and can be axially loaded against said spring bias toward said distal end of said hollow tubular member,
   wherein a fluid path extends longitudinally through said hollow tubular element for guiding the filler, and said at least one cutting blade of said cutter is configured to redirect the filler in a transverse direction relative to said longitudinal axis.

2. A device according to claim 1, wherein:
said piston is axially rotatable within said hollow tubular member.

3. A device according to claim 1, wherein:
said fluid path includes a bore extending through said piston.

4. A device according to claim 3, wherein:
said cutter defines at least one opening in fluid communication with said bore of said piston for redirecting the filler in said transverse direction.

5. A device according to claim 4, wherein:
said transverse direction is a radial direction.

6. A device according to claim 4, wherein:
said at least one cutting blade of said cutter defines said at least one opening.

7. A device according to claim 1, wherein:
said fluid path includes at least one external channel or flute defined by said piston.

8. A device according to claim 1, further comprising:
d) an upper drive body rotationally fixed to said proximal end of said hollow tubular element for rotatably advancing said hollow tubular element into the bone.

9. A device according to claim 8, further comprising:
e) a lower drive body for rotating said cutter and said hollow tubular member, said lower drive body torqueably engaged to said cutter and hollow tubular member only when said cutter is axially loaded against said distal end of said tubular member.

10. A device according to claim 9, wherein:
at least one of said upper drive body and said lower drive body defines at least one radial hole for receiving a torque applying element for facilitating rotation of said device.

11. A device according to claim 1, wherein:
said device further comprises a flexible barb situated at said proximal portion of said device for attachment of a fluid line.

12. A device according to claim 1, wherein:
said hollow tubular element has a diameter that is sized to be advanced into a pilot hole that does not exceed 3.2 mm in diameter.

13. A device according to claim 1, wherein:
said cutter is disc-shaped.

14. A device according to claim 1, wherein:
said cutter defines a plurality of radially-arranged openings in fluid communication with said fluid path.

15. A bone cutting device for cutting maxillary bone and injecting a filler through the maxillary bone and under a subantral membrane to separate the subantral membrane from the maxillary bone and fill the space formed therebetween, the device comprising:
   a) a hollow tubular element extending from a proximal end to a distal end and having a central axis and a threaded exterior surface configured to be threadedly advanced into a hole in bone;
   b) a hollow piston extending within said hollow tubular element;
   c) a cutter mounted to said piston and operably disposed adjacent said distal end of said hollow tubular element wherein said cutter is spring biased into a distally displaced position relative to said distal end of said hollow tubular member, and can be axially loaded against said spring bias toward said distal end of said hollow tubular member; and
   d) a hollow upper drive shaft fluidly and mechanically coupled to a proximal end of said hollow piston,
   wherein said hollow upper drive shaft and said hollow piston define a fluid path for directing filler through said hollow tubular element, and said hollow upper drive shaft rotationally drives said cutter.

16. A device according to claim 15, wherein:
said piston is longitudinally displaceable within said hollow tubular member such that said cutter mounted to said piston is displaceable relative to said distal end of said hollow tubular element.

17. A device according to claim 15, wherein:
said cutter defines at least one opening in fluid communication with said fluid path for redirecting filler in a transverse direction relative to said central axis of said hollow tubular member.

18. A device according to claim 15, further comprising:
e) a lower drive shaft that detachably engages with said hollow upper drive shaft, wherein, said lower drive shaft rotationally drives said cutter when said cutter is in a loaded configuration.

19. A device according to claim 18, wherein:
said upper drive shaft includes a first gear, said lower drive shaft includes a second gear, and said first and second gears are engaged when said cutter is in said loaded configuration, and are disengaged when said cutter is in an unloaded configuration.

20. A device according to claim 19, further comprising:
a spring operably disposed between said first and second gears and biasing said first and second gears toward disengagement and said cutter toward said unloaded configuration.

21. A device according to claim 15, wherein:
said hollow tubular element has a diameter that is sized to be advanced into a pilot hole that does not exceed 3.2 mm in diameter.

22. A device according to claim 15, wherein:
said cutter is disc-shaped.

23. A device according to claim 15, wherein:
said cutter defines a plurality of radially-arranged openings in fluid communication with said fluid path.

* * * * *